United States Patent [19]
McCormick

[11] Patent Number: 5,665,398
[45] Date of Patent: Sep. 9, 1997

[54] APPARATUS FOR EMBEDDING TISSUE SAMPLES

[76] Inventor: James B. McCormick, 6755 Longmeadow Dr., Lincolnwood, Ill. 60646

[21] Appl. No.: 560,653

[22] Filed: Nov. 20, 1995

[51] Int. Cl.$^6$ .................... B29C 39/10; B29C 39/26
[52] U.S. Cl. .................. 425/117; 118/429; 118/500; 249/83; 422/99; 422/102
[58] Field of Search ............... 422/99, 102; 425/117, 425/125; 249/83; 118/429, 500

[56] References Cited

U.S. PATENT DOCUMENTS

| | | | |
|---|---|---|---|
| 3,674,396 | 7/1972 | McCormick | 425/117 |
| 4,557,903 | 12/1985 | McCormick | 422/101 |
| 4,569,647 | 2/1986 | McCormick | 425/117 |
| 4,576,796 | 3/1986 | McCormick | 422/99 |
| 4,623,308 | 11/1986 | Hellon | 249/83 |
| 4,801,553 | 1/1989 | Owen et al. | 118/429 |
| 5,080,869 | 1/1992 | McCormick | 422/102 |
| 5,156,019 | 10/1992 | McCormick | 62/320 |
| 5,269,671 | 12/1993 | McCormick | 425/117 |

*Primary Examiner*—Khanh P. Nguyen
*Attorney, Agent, or Firm*—Fitch, Even, Tabin & Flannery

[57] ABSTRACT

The present invention is directed to a system for providing an embedded tissue specimen subsequent to fluid treatment of the specimen and preparatory to histological examination. The system includes the combination of a cassette for use in the preparation of tissue specimens for histological examination and an embedding mold having a first cavity for receiving the treated specimen and a second cavity for receiving the cassette. The system includes means for dispensing a predetermined amount of molten wax into the embedding mold.

6 Claims, 4 Drawing Sheets

APPARATUS FOR EMBEDDING TISSUE SAMPLES

FIELD OF THE INVENTION

The present invention relates to embedding tissue samples for histological examination and, more particularly, relates to improved methods and apparatus for embedding tissue samples which have been treated by various fluids prior to embedding the tissue samples in paraffin or the like in preparation for microtome slicing and microscopic examination.

BACKGROUND OF THE INVENTION

Standard procedures for preparing tissue samples for microscopic examination involve embedding the tissue sample in paraffin and slicing the paraffin-embedded tissue sample very thinly with a microtome. Prior to embedding the tissue sample, the tissue sample is pre-treated in various solutions appropriate to the examination. Typically, prior to paraffin embedding, the tissue sample is fixed, dehydrated, cleared, infiltrated with molten paraffin and, depending on the test, stained. Such prior treatment of the tissue sample requires subjecting the tissue sample to contact with various fluids, including ethanol, xylene, formaldehyde and water.

A histology laboratory processes a large number of tissue samples for examination and it is important that the tissue samples be prepared as efficiently as possible. A large variety of apparatus has been developed to improve the efficiency of the preparation process. For example, U.S. Pat. No. 3,674,396 to McCormick discloses capsules in which a tissue sample is both prepared for embedding through exposure to various solutions and is then embedded in proximity to the capsule. The '396 McCormick patent discloses a process wherein the tissue sample is statically exposed to the various fluids required for preparation of the tissue samples. In the capsules of the '396 McCormick patent, perforated bottom walls are used to retain the tissue samples while providing access to the tissue samples of the various solutions and finally to molten paraffin.

In previous procedures for processing the tissue sample after subjecting the tissue sample to the various fluids required to treat the sample, molten embedding material is poured into the well of a mold. The treated tissue sample is then removed from the capsule or cassette and is placed into the embedding material in the well of the mold. Molten embedding material is then poured over the tissue sample. The cassette used to process the tissue sample is then placed over the well in the mold and additional molten embedding material is poured into the cassette. After the embedding material solidifies, a cast block is formed that includes the capsule as its base and a protruding portion having the tissue specimen disposed adjacent its front surface. In accordance with standard procedure, the size of various cassettes and capsules which have been developed for processing tissue samples, has been relatively standardized so that the cassette or capsule can be used as the chuck in a microtome slicing device.

U.S. Pat. No. 5,080,869 to McCormick describes a particularly useful cassette for processing tissue samples in a highly efficient manner. The cassette of the '869 McCormick patent is stackable and can be used for preparing a plurality of specimens. The cassette generally includes a plurality of apertures disposed in the walls of the cassette for passage of processing fluids in a direction both orthogonal and parallel to the plane of the bottom wall of the cassette. The cassette also includes a sloping extension of the front wall of the cassette for ease in placing indicia on the cassette for identification of the sample.

It would be desirable to provide an embedding mold for use with the cassette of the type disclosed in the '869 McCormick patent which facilitates embedding the processed tissue sample without incurring problems of previous tissue processing capsules and cassettes wherein the capsule or cassette is placed loosely in an embedding mold and movement of the cassette can occur causing wax to overrun the sides of the cassette. Such excess wax must be flash trimmed to conform the shape of the cassette to the chuck of the microtome which holds the cassette and specimen for cutting. Precision casting would save technical time and improve function.

For example, U.S. Pat. Nos. 4,557,903 and 4,569,647, both to McCormick, disclose improved apparatus for preparing and embedding tissue samples for histological examination. In the '903 McCormick patent, a tissue specimen processing capsule is provided which includes a pair of interlocking frames, each of the frames having a porous web spread across its central opening for holding a tissue specimen in a region divided between the webs. The porous webs permit access to the specimen by processing and impregnating fluids. After the tissue specimen is processed, it is removed from the capsule and placed in a depression of a mold. The empty capsule is placed over the mold depression containing the tissue specimen. Molten paraffin is poured into the mold to fill the depression and to cover the tissue specimen and the porous material of the capsule. The molten paraffin solidifies to form a tissue block with the capsule serving as a clampable base for an outwardly extending, tissue-containing portion.

The '647 McCormick patent discloses an improved method for contacting a tissue specimen with a fluid which is used to treat the tissue specimen. In the '647 McCormick patent, capsules for processing and embedding tissue samples each include a mold, which provides a cavity to receive the tissue sample. The mold has an upper end and a porous or non-porous bottom. The capsule further includes a cover which fits over the open upper end of the mold. The cover includes a frame on which is located a web of porous material intermediate the top and bottom of the frame so that the cover is provided with a recess. The porous web provides access to tissue processing liquids and liquid tissue embedding material, such as paraffin, but prevents passage of any small portions of the tissue specimen which may be generated, thereby preventing cross-contamination of individually capsuled and jointly processed tissue samples. After the tissue samples have been treated with the required fluids, the cover recess above the porous web is at least partially filled with molten paraffin embedding material so that when the embedding material solidifies, the porous web is embedded and the solidified material is thereby formed into a block in the mold. With the porous web and the tissue sample mutually embedded in the block of solidified paraffin, the block is removed from the mold and the cover may be clamped in a microtome and sliced by a microtome blade.

U.S. Pat. No. 5,269,671 to McCormick is directed to a system for providing an embedded tissue specimen subsequent to fluid treatment of the specimen and preparatory to histological examination. The system includes the combination of a cassette for use in the preparation of tissue specimens for histological examination and an embedding mold having a first cavity for receiving the treated specimen and a second cavity for receiving the cassette in an interlocked position overlying the first cavity.

While apparatus and methods for preparing and embedding tissue samples for histological examination have progressed over the years to provide more efficiency in the preparation of tissue specimen, the large number of tissue samples which are prepared daily by histological laboratories, require the most efficient techniques available to increase the number of samples that can be processed and to reduce the cost of such processing.

Accordingly, it is the principal object of the present invention to provide apparatus for use in embedding tissue specimen for histological examination which increases the efficiency of the embedding operation of a specimen and which reduces the cost of preparing tissue samples for microtome slicing and treatment.

Another object of the present invention is to provide an embedding mold for utilization with a cassette to operate in cooperation with such cassette to provide an improved embedding technique.

These and other objects of the invention will become more apparent from the following detailed description and the accompanying drawings.

SUMMARY OF THE INVENTION

The present invention is directed to a system for providing an embedded tissue specimen subsequent to fluid treatment of the specimen and preparatory to histological examination. The system includes the combination of a cassette for use in the preparation of tissue specimens for histological examination and an embedding mold having a first cavity for receiving the treated specimen and a second cavity for receiving the cassette. The system includes means for dispensing a predetermined amount of molten wax into the embedding mold.

DETAILED DESCRIPTION OF THE INVENTION

Figure 1:
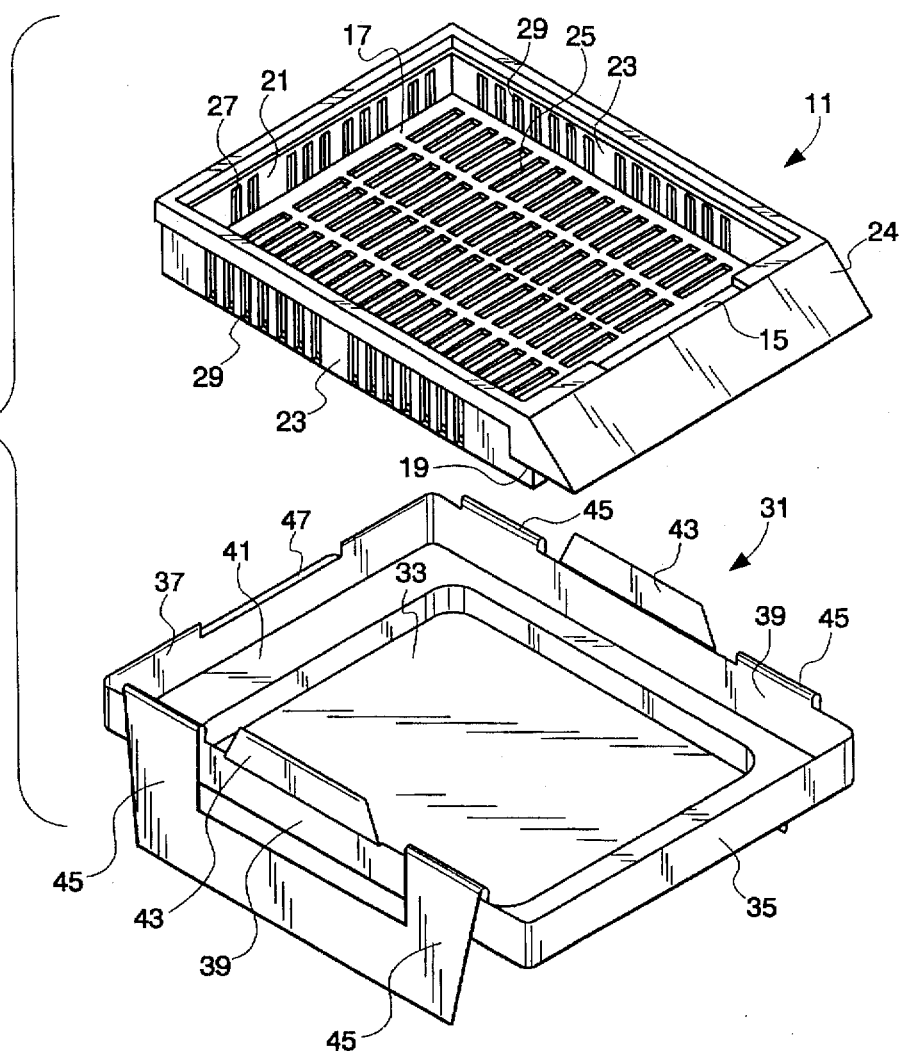
FIG. 1 is a perspective view of the cassette of the invention and the embedding mold for use with the cassette.

As shown in FIG. 1, the cassette 11 comprises a bottom wall 17, a front wall 19, a back wall 21 and two side walls 23. As best seen in FIG. 1 in combination with FIGS. 3–5, an inclined wall 24 extends in a forwardly and downwardly sloping direction from the top of the cassette and away from the front wall 19. The inclined wall 24 is a false wall that is used to facilitate the insertion of indicia on the face of the cassette. An opening 15 in the top of the front wall in the shape of a slot is provided a vent to permit for pumping molten wax into the space between the front wall 19 and the inclined wall 24, as will be discussed hereinbelow.

The bottom wall is provided with a plurality of apertures 25. As shown in the embodiment in FIG. 1, the back wall 21 and front wall 19 are provided with apertures 27 and both of the side walls 23 are provided with apertures 29. All apertures in the side walls are in the shape of slots. The slots have a width of from about 0.020 to about 0.030 inches to provide the capillary pumping of molten wax as discussed hereinbelow. The apertures are provided for the purpose of passing fluid through the cassette at a direction both parallel and orthogonal to the bottom wall 17, as described in the '869 McCormick patent.

An embedding mold 31 is also shown in FIG. 1. The embedding mold 31 has a well 33 for reception of specimen samples after they are processed in the cassette 11. The embedding mold 31 has a front wall 35, a back wall 37 and side walls 39. The back wall 37 and side walls 39 have inner surfaces which generally conform to the outer surface of the back wall and side walls of the cassette 11. The bottom wall 41 of the embedding mold 31 is flat to conform to the flat surface of the bottom wall of the cassette 11. The embedding mold may also be provided with gripping tabs 43 to aid in manipulating the embedding mold. Support runners 45 are provided to stabilize the embedding mold 31 during various embedding operations.

A depressed section 47 of the back wall 37 provides a weir for overflow of molten wax to provide one means for establishing a predetermined amount of molten wax in embedding mold 31. Other means for providing a predetermined amount of molten wax in the embedding mold 31 include the use of a metering pump and use of premeasured aliquots of wax.

Figure 2:
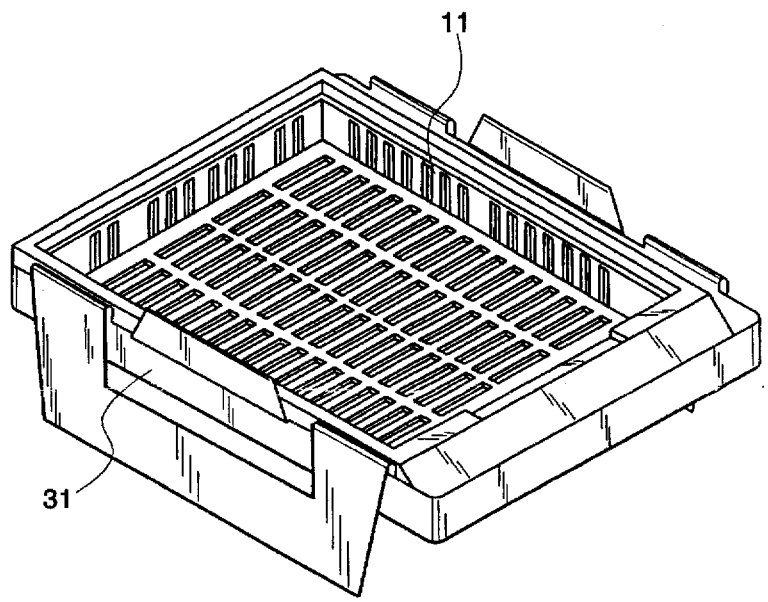
FIG. 2 is a perspective view of the cassette shown inserted into the embedding mold.

FIG. 2 shows the cassette 11 in operating position within embedding mold 31.

Figure 4A:
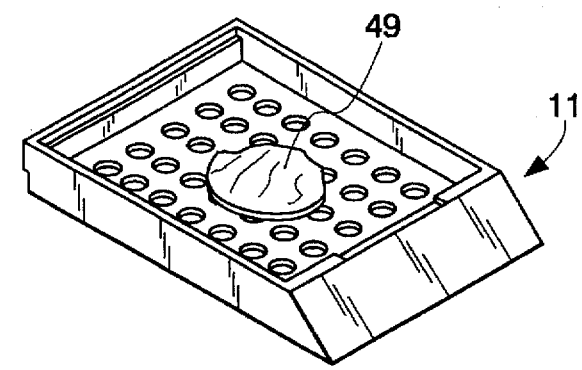
FIGS. 4a, 4b, 4c, 4d, 4e, 4f, and 4g show the sequence of steps used by the prior art to embed tissue samples.
Figure 4B:
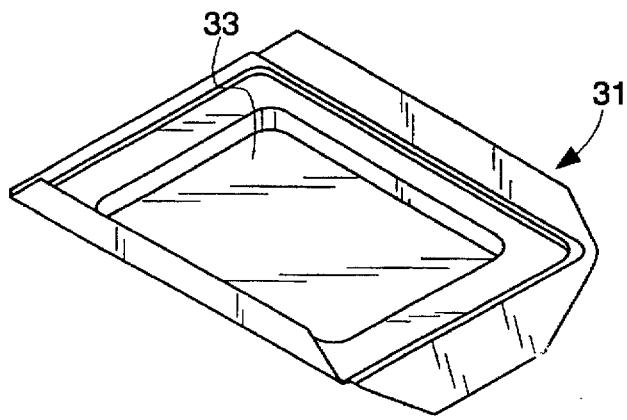
Figure 4C:
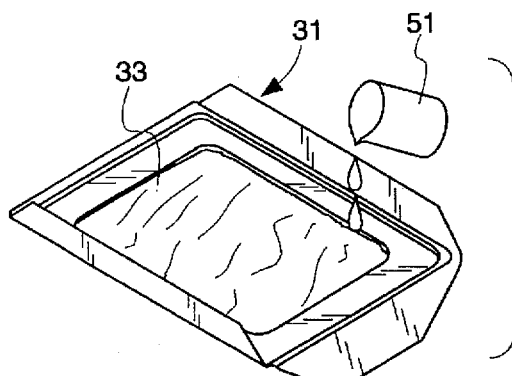
Figure 4D:
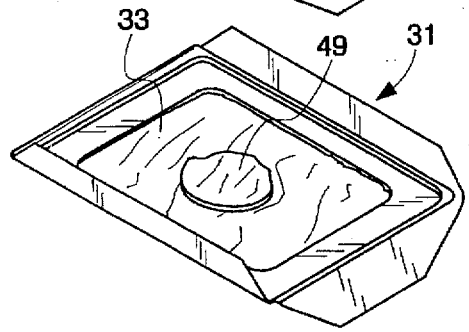
Figure 4E:
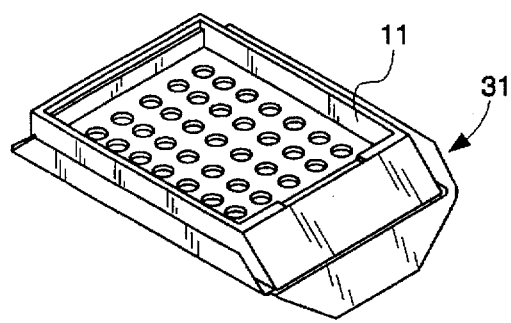
Figure 4F:
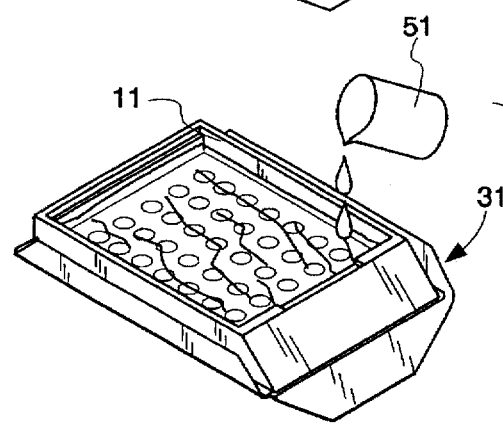
Figure 4G:
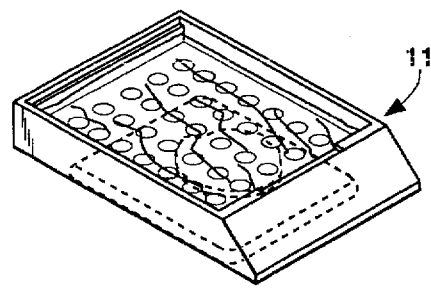

Prior art embedding operations are illustrated in FIGS. 4a–4g. A treated specimen 49 is provided in a cassette 11, as shown in FIG. 4a. An embedding mold 31 is illustrated in FIG. 4b. The embedding mold has a well 33 for receiving the tissue sample 49. Molten wax is poured into the well 33 from a suitable container 51 in a quantity sufficient to fill the well as shown in FIG. 4c. After the molten wax has slightly cooled so as to appear opaque at the bottom of the well 33, the tissue sample 49 is positioned in the wax, as shown in FIG. 4d. The cassette 11 is then placed into position atop the well and the treated sample as shown in FIG. 4e. Additional molten wax is then poured into the embedding mold from a suitable container 51 in a quantity sufficient to cover the bottom of the cassette 11. The finished cassette having the treated tissue sample embedded in crystallized wax on the bottom of the cassette is shown in FIG. 4g.

The problem that exists with the prior art method for embedding tissue samples results from the use of wax in excess of that required and the two-step pouring of the molten wax can result in a weakened wax structure at the interface between the cassette and the well which may result in breaking of the well section from the cassette when the cassette is removed from the embedding mold.

Figure 3:
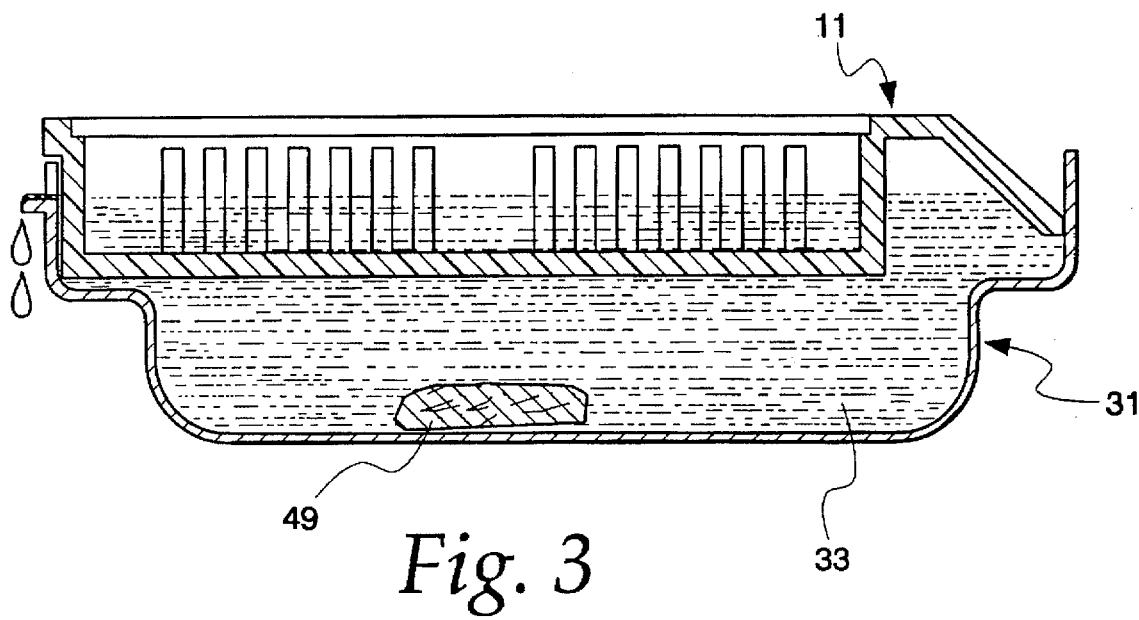
FIG. 3 is a side view taken along line 3—3 of FIG. 5d showing the wax-filled cassette in partial engagement with the embedding mold.
Figure 5A:
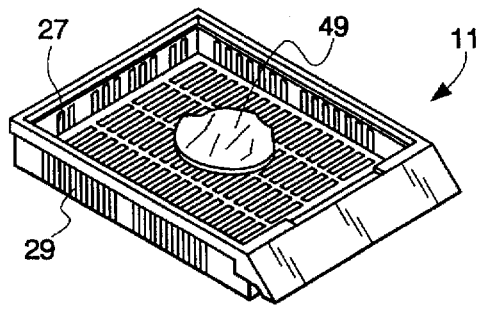
FIGS. 5a, 5b, 5c, 5d and 5e show the sequence of steps used to embed tissue samples in accordance with the embedding system of the present invention.
Figure 5B:
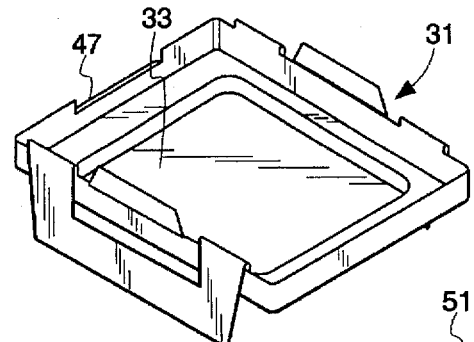
Figure 5C:
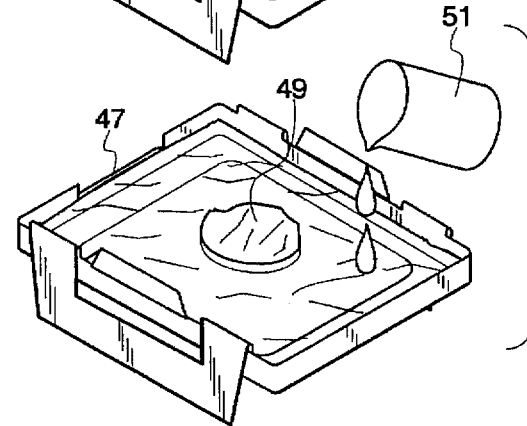
Figure 5D:
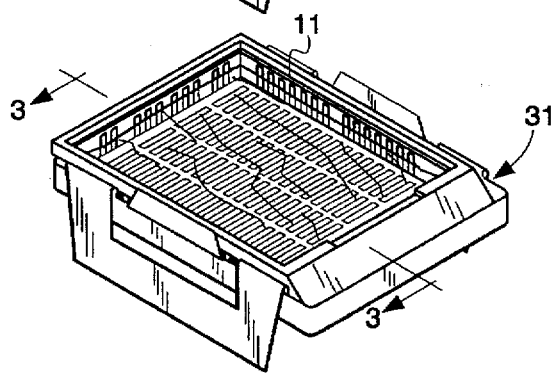
Figure 5E:
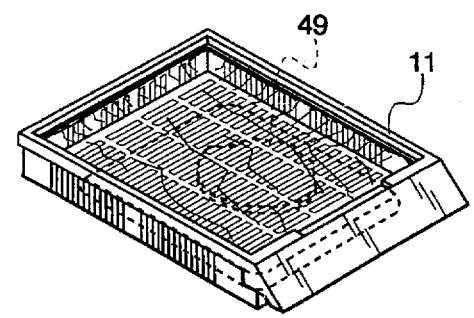

The embedding system of the present invention is illustrated in FIGS. 5a–5e. A treated tissue sample 49 is shown in the cassette 11 of the invention having wall slots 27 and 29. As previously indicated, the slots 27 and 29 have a width of from about 0.020 to about 0.030 inches to provide a capillary pumping of molten wax. An embedding mold 31, as previously described, is illustrated in FIG. 5b. In the system of the present invention, molten wax is poured into the embedding mold until the wax overflows the depressed section 47 which provides a weir for overflow of the wax to deposit a predetermined amount of molten wax in embedding mold 31 as shown in FIG. 5c and FIG. 3. After the bottom of the wax has been slightly chilled, the treated sample 49 is placed into the well 33 of the embedding mold. The cassette 11 is then immediately placed into position in the embedding mold 31 as shown in FIG. 5d.

The slots in the walls of the cassette have a dimension such that the slots act as a capillary pump to draw molten wax from the bottom of the cassette and up the length of the slots so as to fill the slots and the space between the exterior wall of the cassette and the interior wall of the embedding mold. The pumping action provided by the slots is sufficient to pump molten wax over the top of the front wall 19 of the cassette and through the slot 25 in the top wall of the cassette so as to fill the space between the front wall 19 of the cassette and the sloping false wall 24 of the cassette.

The amount of molten wax provided in the embedding mold is sufficient to fill the slot apertures, the spaces between the exterior sides of the cassette walls and the interior sides of the embedding mold walls and the space between the front wall of the cassette and the inclined wall. As best seen in FIG. 3, the initial amount of wax that is poured into the embedding mold is substantially above the floor provided by the bottom wall of the cassette. As the pumping action of the slots continues, this level of wax is drawn down to fill the spaces indicated until it is not substantially above the floor of the cassette. By not substantially above the floor of the cassette is meant that there is no more than about 0.015 to about 0.025 inches of wax remaining above the bottom wall surface after the capillary pumping action has finished.

The embedding system of the present invention simplifies the embedding procedure by requiring only a single pouring of the molten wax. Furthermore, since crystallization of the wax occurs uniformly in the wall spaces and floor openings, there is little risk of separation of the cassette from the embedded specimen during withdrawal of the cassette from the embedding mold, or thereafter when used in microtomy.

While the invention has been described in terms of certain preferred embodiments, modifications obvious to one with ordinary skill in the art may be made without departing from the scope of the invention. Various features of the invention are set forth in the following claims.

What is claimed is:

1. A system for providing an embedded tissue specimen subsequent to fluid treatment preparatory to histological examination comprising the combination of a rectangular cassette having four side walls and a bottom wall for use in the preparation of tissue specimens for histological examination and an embedding mold having a first cavity for receiving the treated specimen and a second cavity having four side walls for receiving said cassette, said cassette having a plurality of slots in each of said four side walls and a plurality of apertures in said bottom wall, said slots having a width sufficiently narrow to cause capillary pumping of molten wax when a predetermined amount of molten wax is dispersed into said embedding mold, said embedding mold having a depressed section in one of the side walls of said second cavity, said depressed section serving as a weir to provide an overflow of an excess of said molten wax to provide said predetermined amount of said molten wax.

2. A system in accordance with claim 1 wherein said predetermined amount of molten wax is sufficient to fill the interior of said wall slots of said cassette and the void space below said weir which exists between the exterior of said walls of said cassette and the interior of said embedding mold side walls by said capillary pumping.

3. A system in accordance with claim 2 wherein said cassette has an inclined false wall extending forwardly and downwardly from the top surface of one of said side walls of said cassette and an aperture in the top of said side wall of said cassette whereby capillary pumping of said molten wax by said slots of said wall of said cassette fills the void space between said inclined wall and said side wall of said cassette through the aperture in the top of said side wall of said cassette, said predetermined amount of molten wax being sufficient to provide molten wax for said interior space filling of said slots of said side walls of said cassette, said void space filling between the exterior of said walls of said cassette and the interior of said walls of said embedding mold and said space between said inclined wall and said side wall of said cassette.

4. A system in accordance with claim 2 wherein said predetermined amount of molten wax is insufficient to leave any substantial amount of molten wax standing above said bottom wall of said cassette after said interior of side wall slots and said void space between said cassette walls and said embedding mold walls are filled.

5. A system in accordance with claim 3 wherein said predetermined amount of molten was is insufficient to leave any substantial amount of molten wax standing above said bottom wall after said interior of said slots of said side wall of said cassette, said void space between said cassette walls and said embedding mold walls and said void space between said inclined wall of said cassette and one of said side walls of said cassette is filled.

6. A system in accordance with claim 1 wherein the width of said slots is from about 0.20 to about 0.30 inches.

* * * * *